United States Patent [19]

Campbell et al.

[11] Patent Number: 5,415,660

[45] Date of Patent: May 16, 1995

[54] IMPLANTABLE LIMB LENGTHENING NAIL DRIVEN BY A SHAPE MEMORY ALLOY

[75] Inventors: Michael P. Campbell, Fridley; Joan E. Bechtold, Minneapolis; Arthur G. Erdman, New Brighton, all of Minn.

[73] Assignee: Regents of the University of Minnesota, Minneapolis, Minn.

[21] Appl. No.: 178,882

[22] Filed: Jan. 7, 1994

[51] Int. Cl.[6] ............................................. A61B 17/56
[52] U.S. Cl. ........................................ 606/62; 606/63; 606/67; 606/68
[58] Field of Search .................................. 606/62-69, 606/72-79, 105

[56] References Cited

U.S. PATENT DOCUMENTS

| | | | |
|---|---|---|---|
| 4,262,665 | 4/1981 | Roalstad | 606/63 |
| 5,059,193 | 10/1991 | Kuslich | 606/63 |
| 5,074,882 | 12/1991 | Grammont | 606/63 |
| 5,156,605 | 10/1992 | Pursley et al. | |
| 5,169,597 | 12/1992 | Davidson | 606/78 |
| 5,180,380 | 1/1993 | Pursley | 606/54 |
| 5,190,546 | 3/1993 | Jervis | 606/62 |
| 5,263,955 | 11/1993 | Baumgart | 606/63 |
| 5,275,599 | 1/1994 | Zbikowski | 606/54 |

FOREIGN PATENT DOCUMENTS

WO9100065 10/1994 European Pat. Off.

OTHER PUBLICATIONS

Anderson, W. V., "Leg Lengthening", *The Journal of Bone and Joint Surgery*, p. 150.

Baumann, F., J. Harms, "Der Verlangerungsnagel", *Archiv für Orthopadische und Unfall-Chirurgie*, 90, 139-146 (1977), J. F. Bergmann-Verlag 1977.

Betz, A., R. Baumgart, L. Schweiberer, "Erstes Voll Implantierbares Intramedullares System zur Callusdistraktion-Marknagel mit Programmierbarem Antrieb zur Beinverlangerung und Segmentverschiebung", *Der Chirurg*, (1990) 61:605-609, Springer-Verlag 1990 (Rough partial translation attached).

Bliskunov, A., "An Implantable Apparatus for Lengthening the Femur Without External Drive", N. N. Priorov Central Research Institute of Traumatology and Orthopedics, Moscow. Crimean Medical Institute, Simferopol. Translated from Meditsinskaya Tekhnika, No. 2, pp. 44-49, Mar.-Apr., 1984, copyright 1984 Plenum Publishing Corporation, pp. 71-76.

Bliskunov, A., "Clinical Results of the Lengthening of the Extremity With Fully Implantable Apparatus".

DeBastiani, Giovanni, et al., "Limb Lengthening by Callus Distraction (Callotasis)", *Journal of Pediatric Orthopedics*, 7:2 (1987), pp. 129-134.

Gotz, J. and W. D. Schellmann, "Kontinuierliche Verlangerung des Femur bei Intramedullarer Stabilisi- (List continued on next page.)

Primary Examiner—Michael A. Brown
Attorney, Agent, or Firm—Leone & Moffa

[57] ABSTRACT

An implantable intramedullary bone lengthening device for correction of limb length deficiencies without a need for transcutaneous connections. The implantable intramedullary bone lengthening nail has an implantable housing, an adjustment mechanism attached to the telescoping cylinder housing, and a drive assembly attached to the housing and the adjustment mechanism for transmitting an expansion force to the adjustment mechanism. The implantable housing may be sealed, encapsulating the unit. The intramedullary bone lengthening nail is inserted into the intramedullary cavity of a bone, which may have been enlarged by reaming. The implantable housing of the intramedullary nail is formed from two telescoping cylinders and is affixed at either end to the bone using pins. The adjustment mechanism is attached to both cylinders of the housing and includes a mechanism for expanding the nail and a ratcheting mechanism for regulating the expansion. The drive assembly includes a shape memory alloy to provide an expansion force. The drive mechanism transmits the expansion force in response to an external signal to the adjustment mechanism.

45 Claims, 11 Drawing Sheets

OTHER PUBLICATIONS crung", *Arch. Orthop. Unfall-chir.* 82, 305–310 (1975), J. F. Bergmann-Verlag Munchen 1975.

Guichet, J. M., P. M. Grammont, and P. Trouilloud, "Intramedullary Nail For Gradual Limb Lengthening: Animal Experimentation", 37th Annual Meeting, Orthopaedic Research Society, Mar. 4–7, 1991, Anaheim, Calif., Department of Bioengineering, Hospital for Joint Diseases Orthopaedic Institute, New York, N.Y. 10003, p. 657.

Helland, Per, "Femoral Elongation by Use of an Elongable Intramedullary Device", Department of Orthopedics and Traumatology, Haukeland University Hospital, N–5021 Bergen, Norway, *Acta Orthop Scand*, 1992:63 (Suppl 247).

Herzenberg, J. E., R. N. Hensinger and S. A. Goldstein, "Michigan Intramedullary Leg Lengthening Nail", The University of Michigan Orthopaedic Surgery Biomechanics, Trauma and Sports Medicine Laboratory, Annual Research Report, Sep. 1989.

Ilizarov, Gavrill A., "Clinical Application of the Tension-Stress Effect for Limb Lengthening", *Clinical Orthopaedics and Related Research*, No. 250, Jan. 1990, pp. 8–26.

Kuo, Paul Pang-Fu, Bei-Chun Yang, Yan-Feng Zhang, Ke—rong Dai, Yue-Fei Yu, "Clinical Use of Nickel-Titanium Shape-Memory Alloy in Orthopedic Surgery—A Preliminary Report", *Progress in Artificial Organs*—1985, ISAO Press, Cleveland 1986, pp. 1105–1107.

Liu, Xiaoping and James D. Stic, "Shape-Memory Alloys and Their Applications", *The Journal of Applied Manufacturing Systems*, Winter 1990, pp. 65–72.

Melton, K. N., "Ni-Ti Based Shape Memory Alloys", *An Introduction to Martensite and Shape Memory*, pp. 20–35.

Monticelli, Giorgio and Renato Spinelli, "Distraction Epiphysiolysis as a Method of Limb Lengthening", *Clinical Orthopaedics and Related Research*, No. 154, Jan.–Feb. 1981, pp. 254–260.

Schollner, D., "Neue Moglichkeiten der Operativen Verlangerung des Oberschenkels", *Z. Orthop.* 110 (1972) 971–974, F. Enke Verlag Stuttgart.

Verkerke, G. J., H. Schraffordt Koops, R. P. H. Veth, J. Oldhoff, H. K. L. Nielsen, "Design of a Lengthening Element for a Modular Femur Endoprosthetic System", *Proc., Instn Mech Engrs*, vol. 203, pp. 97–102.

Verkerke, G. J., et al., "Design of a Load Cell for the Wagner Distractor", *Proc Instn Mech Engrs.*, vol. 203, pp. 91–96.

Wagner, Heinz, "Operative Lengthening of the Femur", *Clinical Orthopedics and Related Research*, No. 136, Oct. 1978, pp. 125–142.

Wayman, C. M., and T. W. Duerig, "An Introduction to Martensite and Shape Memory", Department of Materials of Science and Engineering, University of Illinois at Urbana-Champaign, *An Introduction to Martensite and Shape Memory*, pp. 3–19.

Witt, A. N., M. Jager, "Tierexperimentelle Ergebnisse mit Einem Voll Implantierbaren Distraktionsgerat zur Operativen Beinverlangerung", *Archiv Orthopadische und Unfall-Chirurgie*, 88, 273–279 (1977), J. F. Bergmann-Verlag 1977.

Witt, A. N., M. Jager, "Die Operative Oberschenkelverlangerung Mit Einem Vollimplantierbaren Distraktionsgerat", *Archives of Orthopaedic and Traumatic Surgery*, 92, 291–296 (1978), J. F. Bergmann-Verlag 1978.

Fischer, Carol, William Mackenzie, Robert Meet, Graham Pate, Alastair Younger, Martine Breault, Personal Communication dated Feb. 15, 1992 to Mike Campbell from Carol Fisher, with attachments (7 pages).

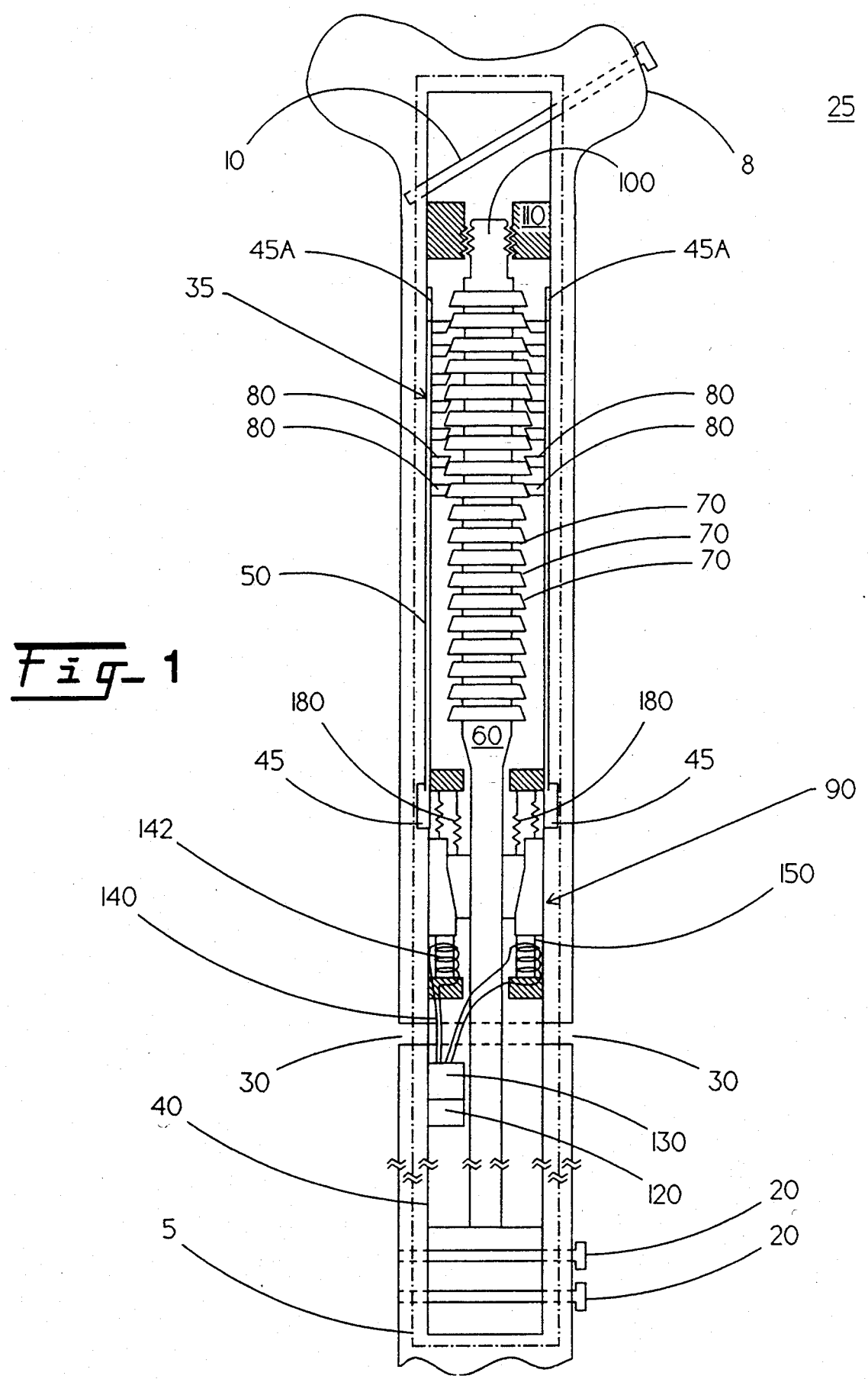
Fig_1

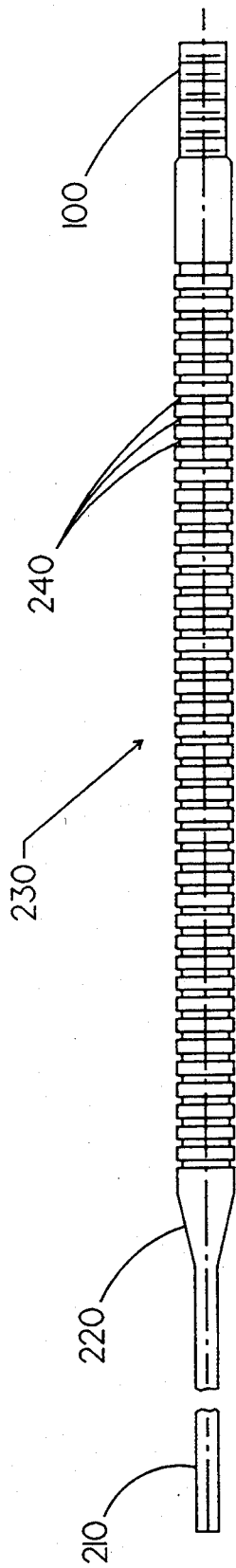
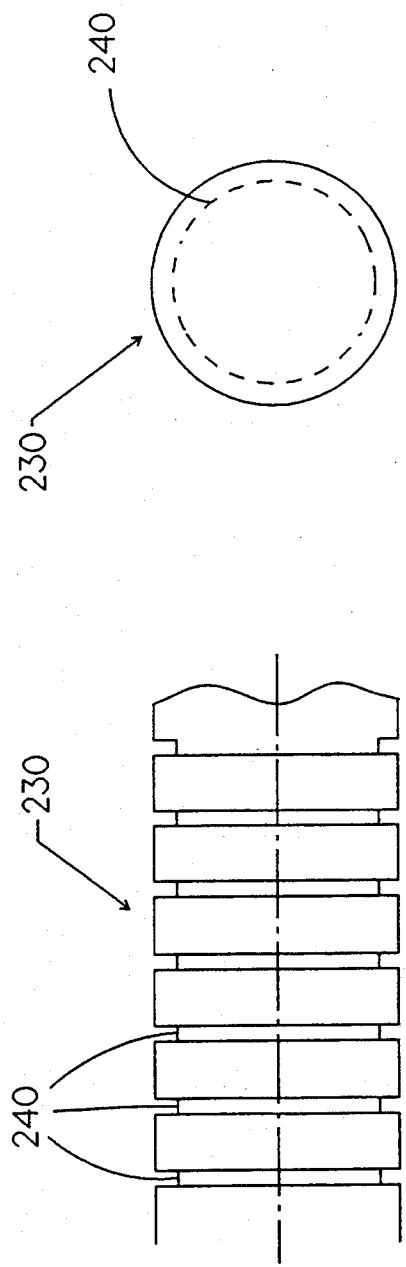

IMPLANTABLE LIMB LENGTHENING NAIL DRIVEN BY A SHAPE MEMORY ALLOY

This invention relates to an intramedullary nail apparatus for lengthening a limb, and more particularly to a orthopedic device powered by a shape memory alloy having no transcutaneous connections.

BACKGROUND OF THE INVENTION

A variety of treatments for leg length discrepancies are known. Leg length discrepancies may arise from birth defects, improper bone growth, disease, or trauma. Such treatments of leg length discrepancies include the use of shoe lifts and special boots to raise the foot in the equinus position. These treatments are simple, but often uncomfortable and aesthetically unattractive, especially in larger leg length discrepancies of 4 cm or more. The field of orthopedics includes other techniques, such as stimulating epiphyseal growth, surgical shortening of the longer limb, and surgical lengthening of the short limb.. As these techniques have developed, the trend has shifted to limb lengthening techniques to treat leg length discrepancies.

Limb lengthening techniques require that the bone of the limb be cut, called an osteotomy or corticotomy. The bone begins development of a callus at this location. The two bone portions are then pulled apart by a mechanical device that is surgically attached to the bone. This procedure is called a distraction, in which the callus is stretched, thereby lengthening the bone.

The current mechanical devices used for limb lengthening are external fixators transcutaneously connected to the bone using wires, pins, or screws. These methods cause such complications as infections at the points of the transcutaneous connections, discomfort in wearing the fixator for the patient, and the unattractive appearance of the fixator. These complications become most evident when the devices are used to lengthen a femur. These problems may be avoided by implanting an internal fixation device inside the bone to perform the distraction.

The "state-of-the-art" limb lengthening technique applies Ilizarov's principle of tension-stress using the Ilizarov external ring fixator with transfixion wires. (Ilizarov, G. A. Clinical application of the tension-stress effect for limb lengthening, *Clin Orthop Rel Res,* 1990; 250:8–26). According to the principle of tension-stress, living tissue subjected to slow, steady tension becomes metabolically activated. Hence, upon the creation of a bone gap and a subsequent distraction of the gap, new bone may be formed to generate an increase in length.

Ilizarov's research indicates that four objectives are especially important in facilitating optimal bone healing. These are:
1. Preservation of the blood supply of the fracture site and the limb as a whole;
2. Preservation of the osteogenic tissue (periosteum, endosteum, and bone marrow) during osteosynthesis and postoperative care;
3. Functional activity of the muscles and joints of the limb; and
4. Early patient mobilization.

Other important objectives are to completely reduce the bone fragments and to provide rigid fixation. Combining these objectives with the principle of tension-stress allows formation of bone not only to heal fractures, but also to correct deformities. The treatment of fractures, pseudarthroses, joint contractures, achondroplasia, and limb length discrepancy are achieved through treatments incorporating these objectives.

Ilizarov's external ring fixation system employs tensioned transfixion wires that pass through the skin and attach to the bone. Based on a study of canine tibiae using this device, Ilizarov formulated the following procedures for maximizing the effectiveness of treatment:
1. corticotomy to preserve marrow and periosteum;
2. stable external fixation;
3. delay before distraction of 5–7 days;
4. distraction rate of 1.0 mm per day;
5. distraction frequency of at least 4 times per day;
6. a period of neutral fixation after distraction;
7. normal function of limb.

The application of these principles may vary according to individual differences and specific characteristics of bone formation. The rate and frequency of distraction may need to be changed during treatment according to the quality of bone being formed. However, these principles are the framework under which most procedures are performed.

The Ilizarov method has been quite successful, but with numerous complications. The device causes serious discomfort for the patient, especially when the device is applied to the femur. The procedure also involves numerous wires that pass through the skin, creating possible infection sites.

The prior art also includes the method of DeBastiani et al., termed callotasis, which is similar to the biological method of Ilizarov. (DeBastiani, G., Aldegheri, R., Renzi-Brivio, L., Trivella, G. Limb lengthening by callus distraction (callotasis), *J Ped Orthop* 1987;7(2):129–134). Instead of a ring fixator, DeBastiani et al. uses a telescoping dynamic axial fixation system where an external monolateral frame is attached to the bone by means of screws. Distraction is performed between 10–15 days after a diaphyseal corticotomy at the rate of 0.25 mm every 6 hours. Upon completion of the desired lengthening amount, the locking screws are removed when consolidation of the callus is determined radiographically. The fixator is removed when corticalization of the new bone is achieved. With this device, DeBastiani et al. reported on 100 lengthenings with a total complication rate of 14%.

Wagner developed a technique which focused on a method of filling the distraction gap with bone. (Wagner, H. Operative lengthening of the femur, *Clin Orthop Rel Res* 1978;(136):125–142). Four Schanz screws are inserted into a bone and attached to a monolateral external fixator. A diaphyseal transverse osteotomy is performed between the 2 sets of screws. The patient carries out distraction at the rate of 1.5 mm per day by turning screws on a monolateral square telescoping apparatus. When the lengthening amount is achieved, the bone is then stabilized with internal fixation and grafted with iliac bone. The distraction apparatus and the Schanz screws are then removed.

Monticelli and Spinelli describe another method called distraction epiphysiolysis that is used to lengthen limbs in patients who are still in the growth stage. (Monticelli, G., Spinelli, R. Distraction epiphysiolysis as a method of limb lengthening. Experimental Study, *Clin Orthop Rel Res* 1981;(154):254–261). This method involves creating a fracture across the epiphyseal plate using a high level of traction. Gradual distraction is accomplished through two pins placed in the epiphysis and the diaphysis. This procedure has the advantages of minimal surgical difficulties and a relatively short treatment time. However this procedure involves a traumatic sudden pain and frequent premature closure of the growth plate.

The above procedures all involve the use of external fixation. Use of external fixation devices have been successful, but have many inherent problems, the most obvious disadvantage being discomfort for the patient. Internal distraction devices avoid many of these problems.

German literature contains the first reports of internal distractors. Schollner reported on a modification to the technique of Anderson by using a distraction device implanted adjacent to the bone being lengthened. (Schollner, D. New ways of operating to lengthen the femur, *Z. Orthop.* 1972;110:971–974 citing Anderson, W. V. Leg lengthening, *J Bone Joint Surg [Br]* 1952;34-b:150). Gotz and Schellmann reported experimental studies on a hydraulic distractor placed in a modified interlocking -nail. (Gotz, J. Schellmann, W. D. Continuous lengthening of the femur with intramedullary stabilization, *Arch Orthop Unfall-Chir* 1975;82:305–310). Their device employed a cylinder external to the bone that supplied hydraulic pressure to an internal nail. Baumann and Harms developed a telescoping nail driven by a threaded spindle transcutaneously attached to the nail. (Baumann, F., Harms, J. The extension nail. A new method for lengthening of the femur and tibia, *Arch Orthop UnfallChir* 1977;90:139–146). Each of these devices employs a connection from an internal device to an external means to drive the distractor.

Witt, et al. is the first report in the prior art on human clinical results from a totally implantable femur distractor. (Witt, A. N., Jager, M., Bruns, H., Kusswetter, W., Hildebrant, J. J. Die operative Oberschenkelverlangerung mit einem vollimplantierbaren Distraktionsgerat, *Arch Orthop Traumat Surg* 1978;(92):291–296). Witt, et al. discloses a device implanted in the soft tissue adjacent to the bone and screwed into the femur proximally and distally. The device of Witt, et al. employs an electric motor housed in the device to generate a distraction force. The motor is controlled by telemetry from outside the body, providing for both forward and backward motion. Witt does not disclose a device implantable in the bone itself or the use of a shape memory alloy to achieve lengthening.

The prior art also includes Bliskunov. (Bliskunov, A. I. An implantable apparatus for lengthening the femur without external drive, *Med Tekhnika* 1984;(2):44–49.) Bliskunov discloses a distractor for intramedullary implantation. Bliskunov discloses a long rod with a rotary ratcheting mechanism that is inserted into the medullary canal following a partial osteotomy. The device of Bliskunov requires a lever is hinged to the long rod and screwed into the wing of the ilium. Bliskunov requires a hip rotation of at least 15° to turn the ratchet wheels of the drive mechanism to achieve lengthening. Each rotation produces 0.04 mm of lengthening, with the movements repeated daily according to a prescribed lengthening rate. Lengthenings of up to 12 cm have been achieved using the Bliskunov device.

Also included in the prior art is international patent WO 91/00065 to Betz et al., filed Jul. 4, 1989, issued Jan. 10, 1991. Betz et al. discloses a fully implantable intramedullary system for lengthening, using telemetry to control an electric motor. Betz et al. postulated that placement of a device in the marrow cavity would not influence healing of a fracture or formation of bone due to callus distraction. Betz et al. reasoned that the nail would not affect the periosteum and that the blood supply comes from the medullar vessels that form around the nail. Betz et al. developed two variants of an intramedullary nail, one with implanted energy and control units, and one with external energy and control units. In the first device, a battery pack and a telemetry receiver are implanted subcutaneously, with an automatic controller. In the second device, only a receiver is implanted and connected to the driving motor, allowing for a much smaller subcutaneous packet. The patient attaches a telemetry sender to their leg during the night, which activates the device and transmits the energy to the motor. Both devices require an electric motor to provide a distraction force. Betz et al. does not disclose a shape memory alloy for providing a distraction force or a ratcheting system for regulating lengthening events.

Guichet et al. developed a device similar to that of Bliskunov, but did not use a lever arm to produce a distraction. (Guichet, J. M., Grammont, P. M., Trouilloud, P. Intramedullary Nail for Gradual Limb Lengthening: Animal Experimentation, *Trans Orthop Res Soc* 1991;16:657). The device of Guichet et al. consists of a stainless steel intramedullary nail with two telescoping tubes connected by a rotary ratcheting mechanism. Guichet requires knee rotations of 30° to trigger the rotary ratchet mechanism, resulting in 0.1 mm of lengthening, with a daily rate of distraction set at 1.24 mm. His initial report described in vivo trials in 10 sheep, completing an average of 6.3 cm of lengthening over 32 days.

U.S. Pat. No. 5,156,605 to Pursley, filed Jun. 11, 1991, issued Oct. 20, 1992, describes an Automatic Internal Compression-Distraction-Method and Apparatus. Pursley discloses two embodiments of an intramedullary telescoping distractor. Like the device of Betz et al., both embodiments require the use of an electric motor and controller to provide a distraction force. Pursley describes two embodiments where the motor and controller are used to drive a lead screw. In the first form, the motor is housed outside the body, and connected to the internal tube by means of a flexible shaft. In the second form, the motor and control units are internally mounted, and controlled by a communication assembly from outside the body. No reports of clinical or experimental use of this device have been found in the literature.

Other limited reports of work on internal lengthening devices include Herzenberg, J. E., Hensinger, R. N., Goldstein, S. A. Michigan intramedullary leg lengthening nail, In: *Biomechanics, Trauma and Sports Medicine Laboratory Annual Report*, University of Michigan, 1989, Verkerke, G. J., Koops, H. S., Verb, R. P. H., Nielsen, H. K. L. Design of a load cell for the Wagner distractor, *Proc Instn Mech Engrs* 1989;203:91–96, Fisher, C. Personal communication. Feb. 12, 1992, and Hellend, P. Femoral elongation by use of an elongable intramedullary device, *Acta Orthop Scand* 1992;63(Suppl 247):16. The following table is a summary of research work done on internal lengthening devices with implantable drive mechanisms.

| NAME | YEAR | DRIVE MECHANISM |
|---|---|---|
| Witt, et al. | 1978 | Electric Motor |
| Bliskunov | 1984 | Hip Rotation |

-continued

| NAME | YEAR | DRIVE MECHANISM |
| --- | --- | --- |
| Herzenberg, et al. | 1989 | N/A |
| Verkerke, et al. | 1989 | Electric Motor (endoprosthesis) |
| Betz, et al. | 1990 | Electric Motor |
| Fisher, et al. | 1992 | Electric Motor |
| Guichet, et al. | 1991 | Hip Rotation |
| Hellend | 1992 | Leg Rotation |
| Pursley, et al. | 1992 | Digital Motor |

While the prior art shows various intramedullary nails for limb lengthening, the prior art does not include the use of shape memory alloys as a expansion force generation means. To trigger lengthening events, the prior art has relied on mechanical input from the patient or an electric motor to provide a distraction force. In the case of mechanical input, this reliance may require a transcutaneous connection or additional connections to bones other than the bone being lengthened to provide mechanical displacement. The use of a motor to provide distraction force may require that a larger package be implanted. The use of a shape memory alloy to provide a distraction force may avoid these disadvantages.

A shape memory alloy (SMA) is a material having an ability to "remember" a certain shape after significant deformation. Two phases of materials possessing the shape memory effect, austenite and martensite, provide for this property. These phases have significantly different moduli of elasticity and occur at different temperatures. Martensite is a low temperature, low modulus phase. Austenite is a higher temperature, high modulus phase.

Fabrication of an alloy possessing the shape memory effect is a combination of mechanical deformation and temperature change. The "memory shape" of the alloy is set in the austenite phase. The alloy is subsequently cooled to the martensite phase and deformed. Subsequent heating of the alloy restores the original memory shape and recovers the deformation. The alloy is under high strain in the martensite phase, and under low strain in the austenite phase.

A two-way shape memory effect (TWSM) occurs when a SMA returns to the deformed martensite shape upon cooling from austenite. A special treatment process called training biases the martensite structure to form the same shape each time upon cooling, resulting in the TWSM effect. As a result, the SMA may not require a resetting force to achieve cycling as does the "one-way" alloy.

Whereas the one-way and two-way effects are thermally activated, superelasticity is a mechanical type of shape memory. One method of fabricating a superelastic material is to deform the material in an austenire phase, above the martensite start temperature ($M_s$). The resulting stress causes the martensite phase to become more stable than the austenite phase and results in a martensite transformation, called stress-induced martensite (SIM). When the stress is released, the martensite becomes unstable and the original shape is fully recovered.

A number of industries use shape memory alloys. One popular application of shape memory alloys is in tube couplings. Medical applications such as guide wires and orthodontic arch wires use shape memory alloys because of their properties of superelasticity and high shape recovery, and because of their ability to provide low, continuous forces. The ability of shape memory alloys to exert a force after implantation and exposure to body temperature make them useful in orthopedic applications such as staples, screws, nails, and femoral cups.

Shape memory alloys provide distinct advantages over the prior art. Biocompatible shape memory alloys are available. Furthermore, shape memory alloys that provide sufficient force for distraction may be contained within a small package within the intramedullary nail apparatus. Shape memory alloys may be molded to fit within necessary parameters.

It is therefore a motive of the invention to provide for an intramedullary nail apparatus that may be encapsulated, provides a shape memory alloy for an expansion force and a drive mechanism for transmitting motion and force to accomplish distraction of a bone, and that may be electrically activated without the need for mechanical input from a patient.

SUMMARY OF THE INVENTION

The invention provides an intramedullary nail apparatus for suitable fixation and distraction without the use of any transcutaneous attachments. The invention has an implantable drive mechanism comprised of a shape memory alloy attached to an inner cylinder and an outer telescoping cylinder that are arranged to form the housing of the intramedullary nail. The drive mechanism provides an expansion force in response to an external signal powered by the shape memory alloy. The drive mechanism also includes a mechanical displacement control that regulates the expansion and provides a controlled expansion of the intramedullary nail apparatus. The inner cylinder and outer telescoping cylinder are affixed to the bone, thus providing for an appropriate distraction of the bone during expansion.

It is one object of the invention to provide a intramedullary nail apparatus that allows for distraction without the use of transcutaneous attachments or an external fixation device.

It is another object of the invention to provide an intramedullary nail apparatus that is powered by a shape memory alloy housed within the apparatus.

It is yet a further object of the invention to provide an intramedullary nail apparatus that provides an accurately controlled distraction by precise increments.

It is yet a further object of the invention to provide an intramedullary nail apparatus that is encapsulated.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

FIG. 1 shows a perspective view of one embodiment of the intramedullary nail apparatus of the invention.

FIG. 4A shows a schematic view of a push rod of the intramedullary nail apparatus of the invention.

FIGS. 4B and 4C show a schematic view of a portion of a push rod having a plurality of grooves as employed in one example of the invention.

DETAILED DESCRIPTION OF THE PREFERRED EMBODIMENT

Figure 2A:
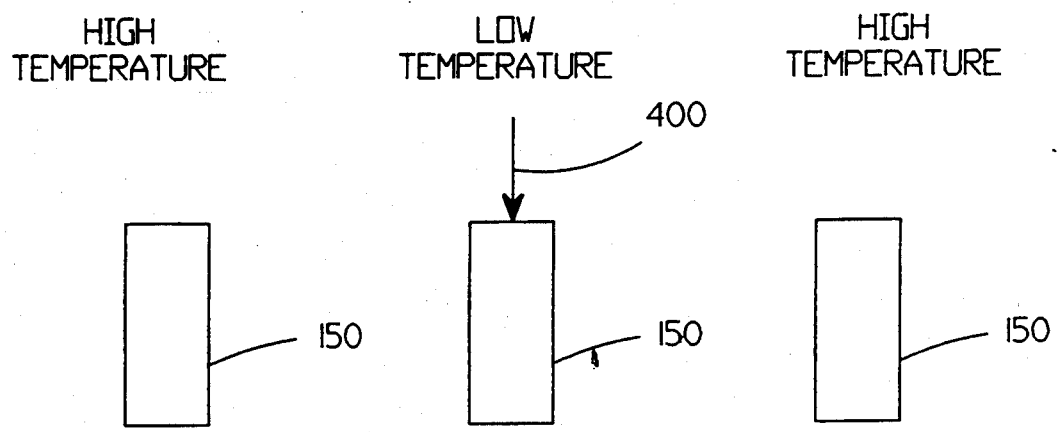
FIG. 2A shows a diagram of the different states of a shape memory driver.

Referring now to FIG. 1, FIG. 1 shows a perspective view of one embodiment of the intramedullary nail apparatus of the invention. The apparatus of the invention has a housing 35 and a drive mechanism 90. The apparatus of the invention is inserted into a marrow cavity 5 of a bone 8. The intramedullary nail 25 is positioned along the length of the bone 8, allowing the housing 35 of the intramedullary nail 25 to contact the bone 8 along a portion of the inside of the cavity 5. The intramedullary nail 25 is attached to the bone 8 by a proximal interlocking bolt 10 and distal interlocking bolts 20 on either side of the site of a corticotomy or osteotomy 30. The housing 35 of the intramedullary nail 25 comprises an inner cylinder 40 and a telescoping outer cylinder 50, allowing for distraction in response to the impetus of the drive mechanism 90. A seal 45 joins the inner cylinder 40 and the telescoping outer cylinder 50. The seal 45 also preserves the integrity of the intramedullary nail 25 and prevents body fluids from entering the housing 35. A second seal 45A may serve as a backup to preserve the integrity of the intramedullary nail 25 if seal 45 fails. The second seal 45A may also cooperate with the seal 45 to lower the pressure differential between chambers resulting in an improved seal.

The inner cylinder 40 houses the drive mechanism 90, which comprises a push rod 60, a plurality of flexible rings 70, a plurality of circular ledges 80, and a drive assembly 90. The push rod 60 is located within the inner cylinder 40 and passes through the drive assembly 90. The plurality of flexible rings 70 are attached to the push rod 60. As the drive assembly 90 provides a proximal thrust to the push rod 60, the plurality of flexible rings 70 engage a plurality of circular ledges 80 attached to an inner wall of the inner cylinder 40. The flexible ring 70 and circular ledge 80 system form a ratchet assembly, allowing the push rod 60 to move in a proximal direction, while prohibiting distal movements. The proximal end of the push rod 60 forms a screw 100 that attaches the push rod 60 to an internal thread 110 fixed to the telescoping outer cylinder 50. Thus, when the drive mechanism 90 is activated, the intramedullary nail 25 is expanded and provides a suitable distraction force to the bone 8.

In one embodiment, telemetry initiates lengthening events and controls activation of the drive assembly 90. An external transmitter sends a signal to a receiver 120 enclosed in the inner cylinder 40. The receiver 120 activates a power supply 130 also enclosed in the inner cylinder 40. The power supply 130 supplies a current to a resistance wire 142 wrapped around the shape memory driver 150. The resistance wire 142 heats as current is passed through it and transfers heat to the shape memory driver 150, providing for shape recovery and expansion of the shape memory driver 150. In an alternate embodiment of the invention, the shape memory driver 150 serves as a resistive element in place of resistance wire 142 and the shape memory driver 150 heats up as current is passed through it. If the shape memory driver 150 is fabricated to possess one-way thermal recovery properties, biasing elements 180 return the shape memory driver 150 to a deformed condition. If the shape memory driver 150 is fabricated to possess two-way thermal properties, then the shape memory driver 150 automatically resets during cooling.

In another embodiment of the invention, the receiver 120 and the power supply 130 are located in a subcutaneous packet outside of the intramedullary nail apparatus and supply current to the shape memory driver 150 by wires 140. Power supply 130 may advantageously comprise either a battery, a capacitor, or both. If the power supply 130 comprises a capacitor, power may be transferred to the capacitor by telemetry to be stored until used. Alternatively, the battery may charge a capacitor that provides current to the shape memory driver 150.

FIG. 2A shows a diagram of the different states of the shape memory driver 150. FIG. 2A shows the fabricated shape of the shape memory driver 150. The shape memory driver 150 is fabricated under conditions of high temperature and low strain in a state called the austenite phase. The shape memory driver 150 may be cooled and subjected to a strong force indicated as force 400, resulting in a state called the martensite phase and leaving the shape memory driver 150 under a high strain. After subjection to high heat, the shape memory driver 150 may regain its original shape.

Figure 2B:
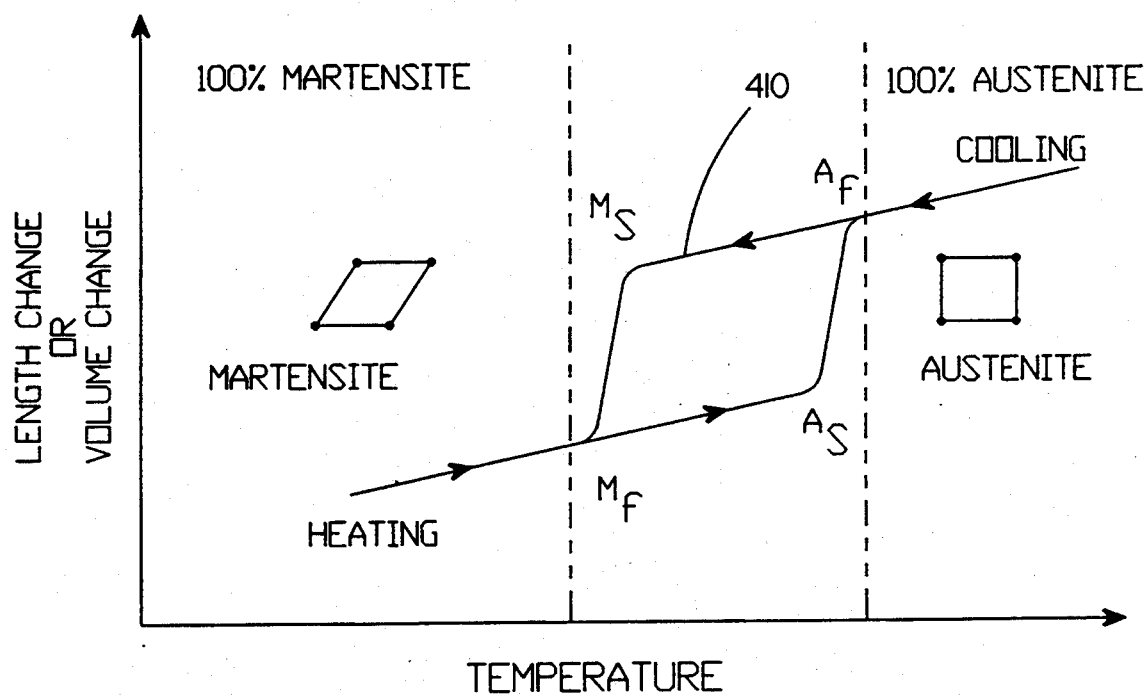
FIG. 2B shows a graph of length change v. temperature change for a shape memory driver.

FIG. 2B shows a graph of length change v. temperature change for the shape memory driver 150. The graph generally illustrates the correlation of property changes of the shape memory driver 150 with temperature. A resetting force to restore the shape memory may or may not be needed depending on the process used to fabricate the shape memory driver 150. The shape memory driver 150 may be advantageously fabricated to return to the martensite phase during cooling as indicated by curve 410.

Figure 3:
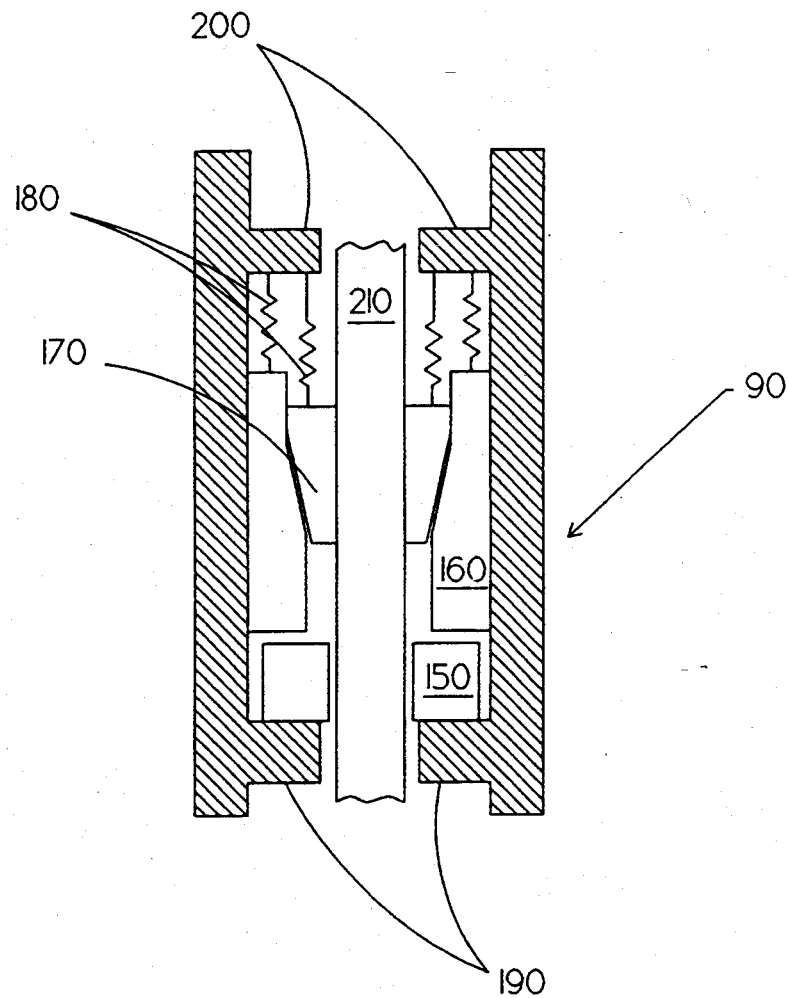
FIG. 3 shows a schematic view of the elements of a drive assembly of the intramedullary nail apparatus of the invention.

FIG. 3 shows a schematic view of the elements of the drive assembly 90 of the intramedullary nail apparatus of the invention. The drive assembly 90 comprises a shape memory driver 150, a push collar 160, a wedge gripper 170, and biasing elements 180. The inner cylinder 40 has a distal strut 190 and proximal strut 200 that house the drive assembly 90. The shape memory driver 150 is secured on the distal strut 190. The push collar 160 is located above the shape memory driver 150. The biasing elements 180 are attached to the proximal strut 190 and the push collar 160. The biasing elements 180 bias the push collar 160 toward the shape memory driver 150 to ensure stable contact with the shape memory driver 150. A shaft 210 of the push rod 60 passes through the drive assembly 90 and through the wedge gripper 170 situated within the push collar 160. The biasing elements 180 also attach to the wedge gripper 170 and bias the wedge gripper 170 within the push collar 160. The biasing force combined with the angle of the push collar 160 cause the wedge gripper 170 to grip the shaft 210 of the push rod 60. The attachment of the wedge gripper 170 to the shaft 210 of the push rod 60 forces the push rod 60 to move with the drive assembly 90.

Telemetry activates the shape memory driver 150. The shape memory driver 150 forces the drive assembly 90 in a proximal direction during activation. The biasing elements 180 act to prevent the drive assembly 90 from jamming during activation and to maintain the attachment of the wedge gripper 170 to the shaft 210 of the push rod 60. The proximal movement of the drive assembly 90 drives the push rod 60 up through the ratchet assembly and forces a proximal movement of the outer cylinder 50, thus expanding the intramedullary nail 25 and providing an appropriate distraction.

FIG. 4A shows a schematic view of the push rod 60 of the intramedullary nail apparatus of the invention. The push rod 60 has a shaft 210, a tapered section 220, a grooved shaft 230, and a screw 100. The shaft 210 of the push rod 60 forms the distal end of the push rod 60 and is inserted within the inner cylinder 40 and passes through the drive assembly 90. A tapered section 220 links the shaft 210 to the grooved shaft 230 and increases the diameter of the push rod 60 from the shaft 210. The grooved shaft 230 is located on a proximal section of the push rod 60, and has a plurality of grooves 240 into which the plurality of flexible rings 70 are inserted. The proximal end of the push rod 60 forms a screw 100. The screw 100 attaches to the internal thread 110 of the outer cylinder 50, and forces the outer cylinder 50 to move with the push rod 60.

FIGS. 4B and 4C show a schematic view of a portion of the push rod 60 having a plurality of grooves 240 as employed in one embodiment of the invention. The proximal section of the push rod 60 include the plurality of grooves 240. The plurality of grooves 240 accommodate insertion of the plurality of flexible rings 70. As may be seen with reference to FIG. 5, fabrication of the plurality of grooves 240 provides for an appropriate size to allow the plurality of flexible rings 70 to flex inwardly when sliding past the plurality of circular ledges 80. The plurality of grooves 240 also allow the plurality of flexible rings 70 to rest on the plurality of circular ledges 80 when bearing a load.

Figure 5:
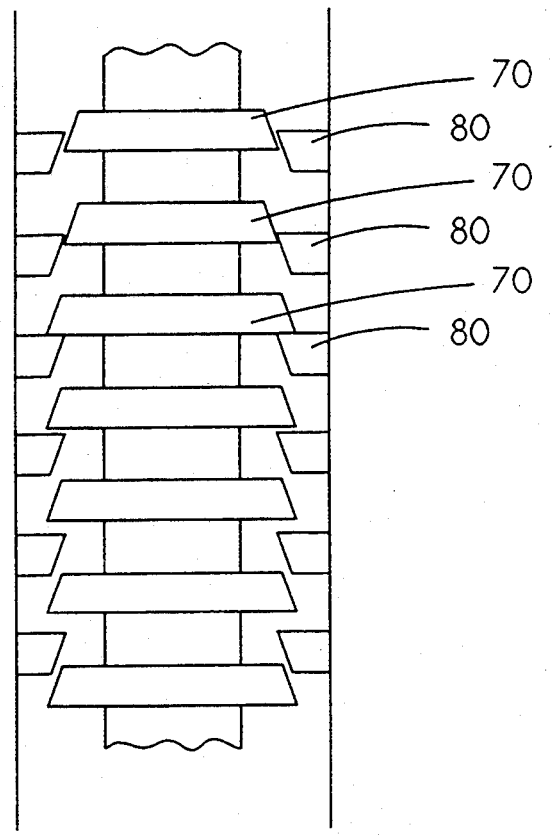
FIG. 5 shows a schematic view of a portion of a ratcheting mechanism of the intramedullary nail apparatus of the invention.

FIG. 5 shows a schematic view of a portion of the ratcheting mechanism of the intramedullary nail apparatus of the invention. The ratchet assembly comprises the plurality of flexible rings 70 and the plurality of circular ledges 80. The plurality of flexible rings 70 and the plurality of circular ledges 80 engage in a staggered manner, allowing for smaller increments of movement and precise lengthenings of the intramedullary nail 25. As each of the plurality of flexible rings 70 engages the plurality of circular ledges 80, each flexible ring 70 is deflected inward, as further described in FIG. 6A, 6B, and 6C. After the flexible ring 70 passes a circular ledge 80, the flexible ring 70 comes to rest in a position to bear a load. In one example embodiment of the invention, the plurality of circular ledges 80 are spaced about 0.25 mm apart less than the spacing of the plurality of flexible rings 70, allowing for incremental displacements of about 0.25 mm. The plurality of ledge-ring assemblies allow for a total lengthening of about 80 mm.

Figure 6A:
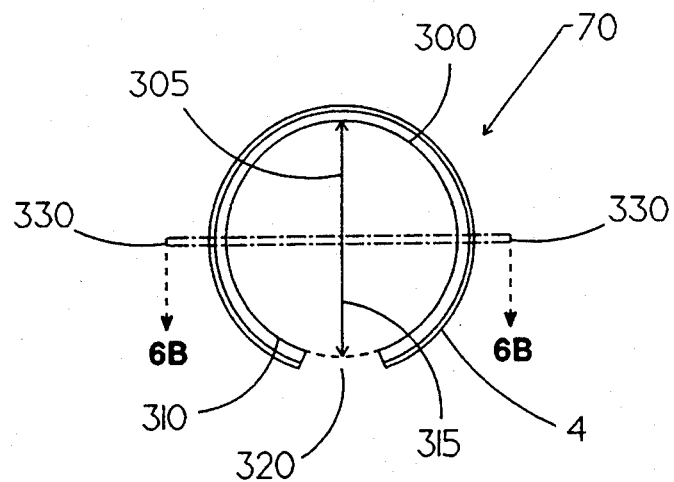
FIGS. 6A and 6B show schematic views of the top and cross section of a flexible ring of the invention.
Figure 6B:
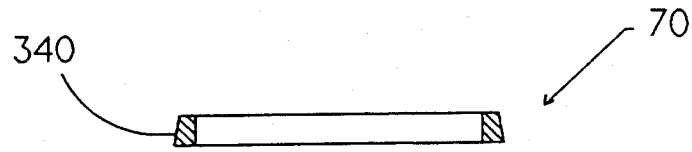

FIGS. 6A and 6B show a schematic view of the top and cross section of the flexible ring 70 of the invention. The flexible ring 70 is made from a flexible material and has an upper half 300 and a lower half 310. The flexible material may be a flexible material known to be suitable for use in implantable devices. Such materials are known in the art. The upper half 300 and the lower half 310 have an upper radius 305 and a lower radius 315. The lower half 310 of the flexible ring 70 also has a gap 320. The lower radius 315 is larger than the upper radius 305 and is separated from the upper radius by an offset 330. The upper radius 305 is formed to fit tightly around the plurality of grooves 240 in the push rod 60. The offset 330 and the larger lower radius 315 allow the lower half 315 of the flexible ring 70 to fit loosely around the plurality of grooves 240 in the push rod 60. The side view shows that the flexible ring 70 has a taper 340. The taper 340 provides a sliding surface for the flexible ring 70 and provides an inward force on the flexible ring 70 as the flexible ring 70 is moved upwards. The offset 330 and the larger lower radius 315 allow the flexible ring 70 to deflect inward and narrow the gap 320, decreasing the diameter of the flexible ring 70, and allowing the flexible ring 70 to pass the circular ledge 80.

Figure 6C:
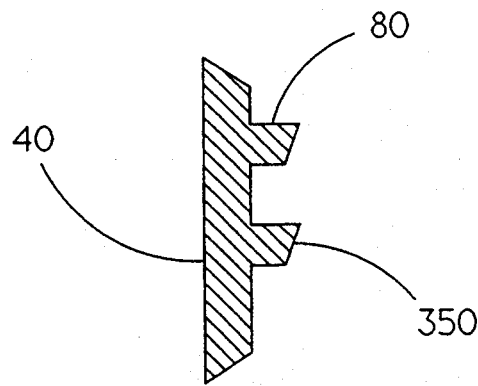
FIG. 6C shows a schematic view of a portion of a plurality of circular ledges of the invention.

FIG. 6C shows a schematic view of a portion of the plurality of circular ledges 80 of the invention. The plurality of circular ledges 80 is fixed to an inner wall of the inner cylinder 40. The plurality of circular ledges 80 is arranged so that the plurality of circular ledges 80 engage the plurality of flexible rings 70 in a staggered fashion. The plurality of circular ledges 80 have a taper 350, approximately equivalent to the taper 340 of the flexible ring 70. When engaged, the taper 340 provides for an inward force on the flexible ring 70 for inward deflection.

Figure 7A:
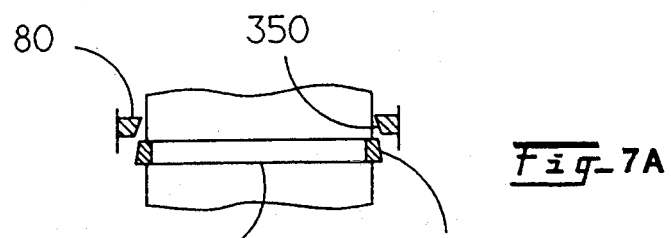
FIGS. 7A, 7B and 7C show a schematic view of an operation of a portion of the ratcheting assembly of the invention.
Figure 7B:
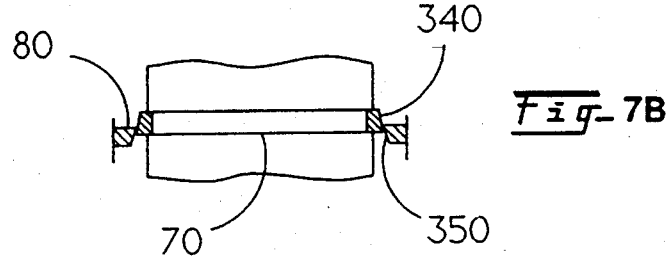
Figure 7C:
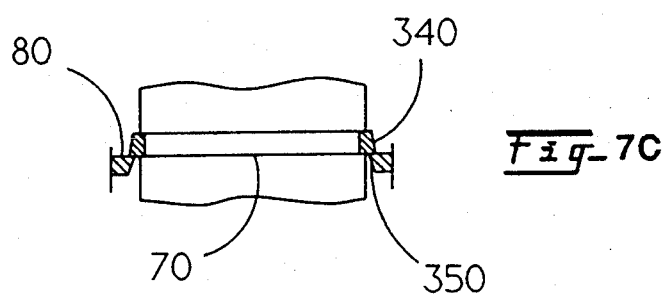

FIGS. 7A, 7B and 7C show a schematic view of the operation of a portion of the ratcheting assembly of the invention. The ratcheting assembly has a plurality of flexible rings 70, a push rod 60, and a plurality of circular ledges 80. The plurality of flexible rings 70 is affixed to the push rod 60 within a plurality of grooves 240. The plurality of circular ledges 80 are fixed to the inner wall on the inner cylinder 40. During operation, the plurality of flexible rings 70 engage the plurality of circular ledges 80. FIG. 7A shows the flexible ring 70 while unengaged with the circular ledge 80 in a free sliding state. FIG. 7B shows the flexible ring 70 while sliding past the circular ledge 80 in an inward deflection state. The taper 340 of the flexible ring 70 and the taper 350 of the circular ledge 80 act to induce the inward deflection state. FIG. 7C shows the flexible ring 70 resting on the circular ledge 80 in a position to assume a weight bearing load.

Figure 8A:
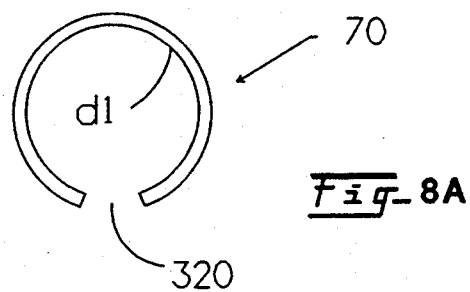
FIGS. 8A and 8B show a schematic view of an operation of the flexible ring of the invention.
Figure 8B:
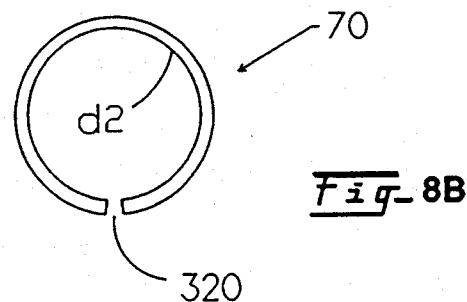

FIG. 8A and 8B show a schematic view of the operation of the flexible ring 70 of the invention. FIG. 8A shows a first diameter d1 of the flexible ring 70 when in the free sliding state or when resting on the circular ledge 80. FIG. 8B shows a second diameter d2 of the flexible ring 70 when in the full inward deflected state. The smaller second diameter d2 of the inward deflected state allows the flexible ring 70 to deflect past the circular ledge 80.

Figure 9A:
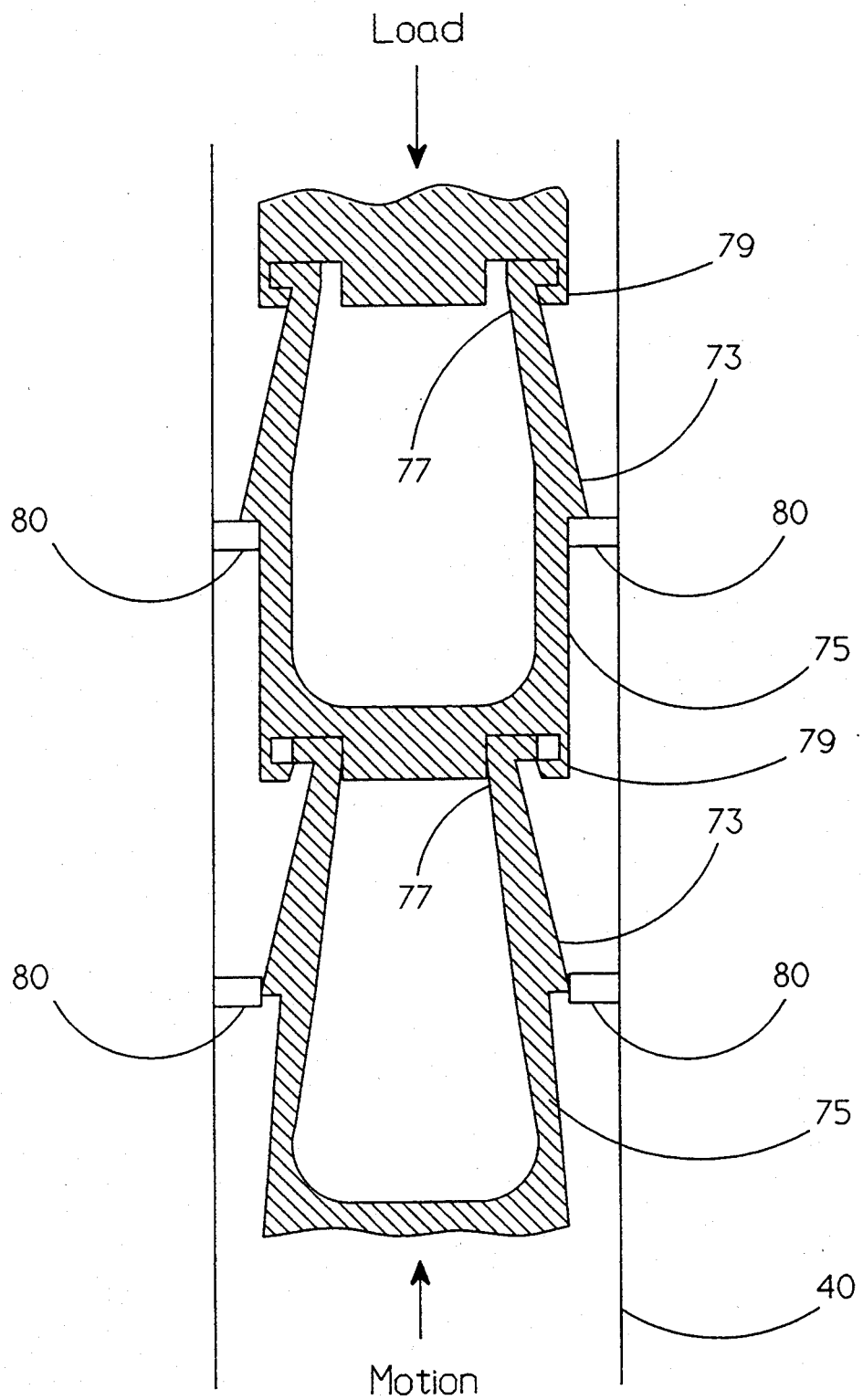
FIGS. 9A and 9B show schematic views of alternate embodiments of a ratcheting assembly of the invention.
Figure 9B:
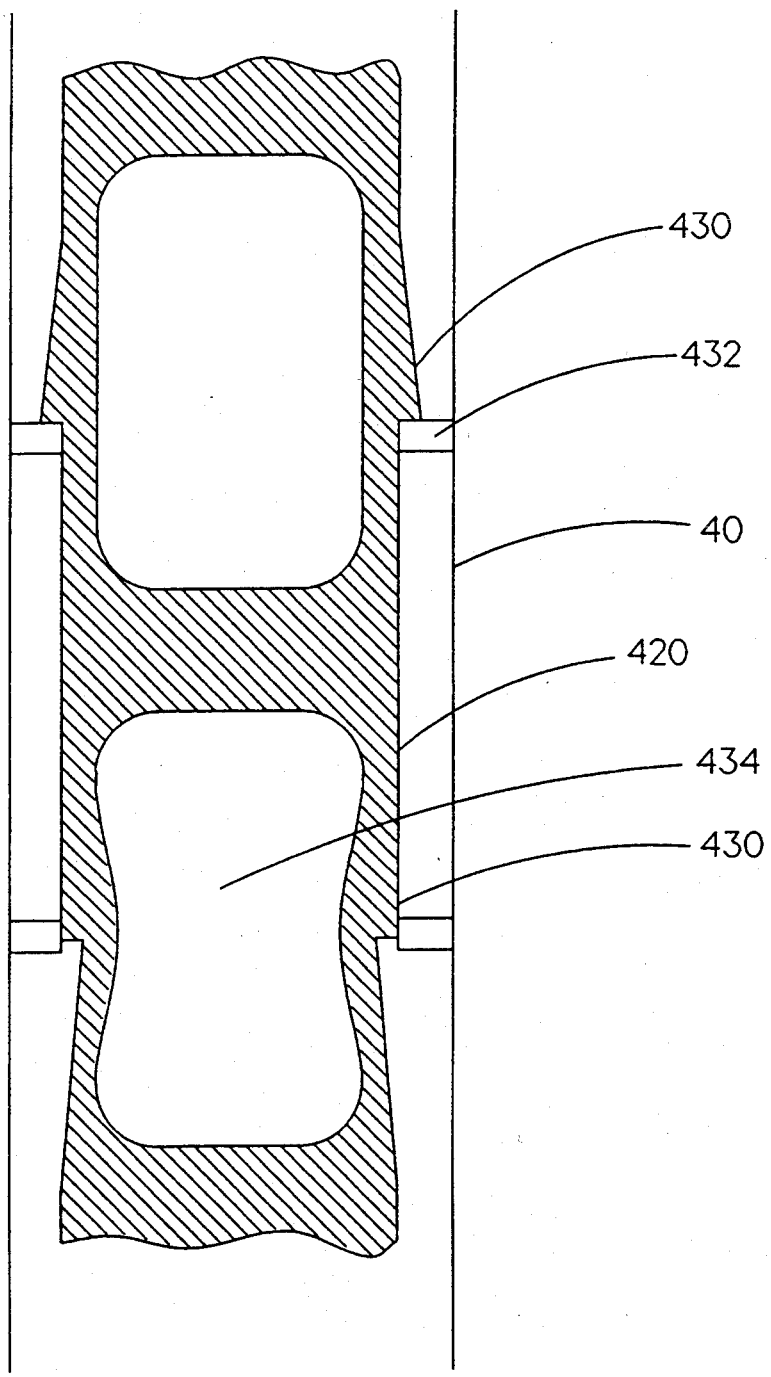

FIGS. 9A and 9B show schematic views of alternate embodiments of the ratcheting assembly of the invention. FIG. 9A shows a schematic view of a cantilever flexible rod ratchet system. The ratcheting assembly has a plurality of flexible hooks 75 engaging a plurality of circular ledges 80. The plurality of flexible hooks 75 comprise a series of separate elements linked top to bottom. The top of each element comprises a hook 77, and the bottom of each element comprises a catch 79. The hook 77 of each element of the plurality of flexible hooks 75 is connected to the catch 79 of each next element. In addition, each element of the plurality of flexible hooks 75 has a taper 73. The taper 73 promotes the deflection of each element of the plurality of flexible hooks 75 past the plurality of circular ledges 80. During deflection, the hook end 77 of the element deflects inward. The plurality of flexible hooks 75 attach at a distal end to the shaft 210 of the push rod 60 driven by the drive assembly 90. The plurality of flexible hooks 75 attach at a proximal end to the telescoping outer cylinder 50 by the screw 100. The plurality of circular ledges 80 are attached to the inner wall of the inner cylinder 40. The plurality of flexible hooks 75 engage the plurality of circular ledges 80 and regulate the expansion of the intramedullary nail 25 similarly to the ratcheting mechanism of the plurality of flexible rings 70. However, each of the plurality of flexible hooks 75 is a separate element, allowing the plurality of flexible hooks 75 to be individually flexible, and to accommodate curves.

FIG. 9B shows a schematic view of a fixed end flexible rod ratcheting system. The fixed end flexible rod ratcheting system has a flexible rod 420 having a plurality of hooks 430. The plurality of hooks 430 engage a plurality of circular ledges 432 mounted on an inner wall of an inner cylinder 40 in a staggered pattern. The flexible rod 420 has a plurality of cavities 434 that promote deflection by bending inward during axial displacement, allowing the plurality of hooks 430 to move past the plurality of circular ledges 432.

Figure 10:
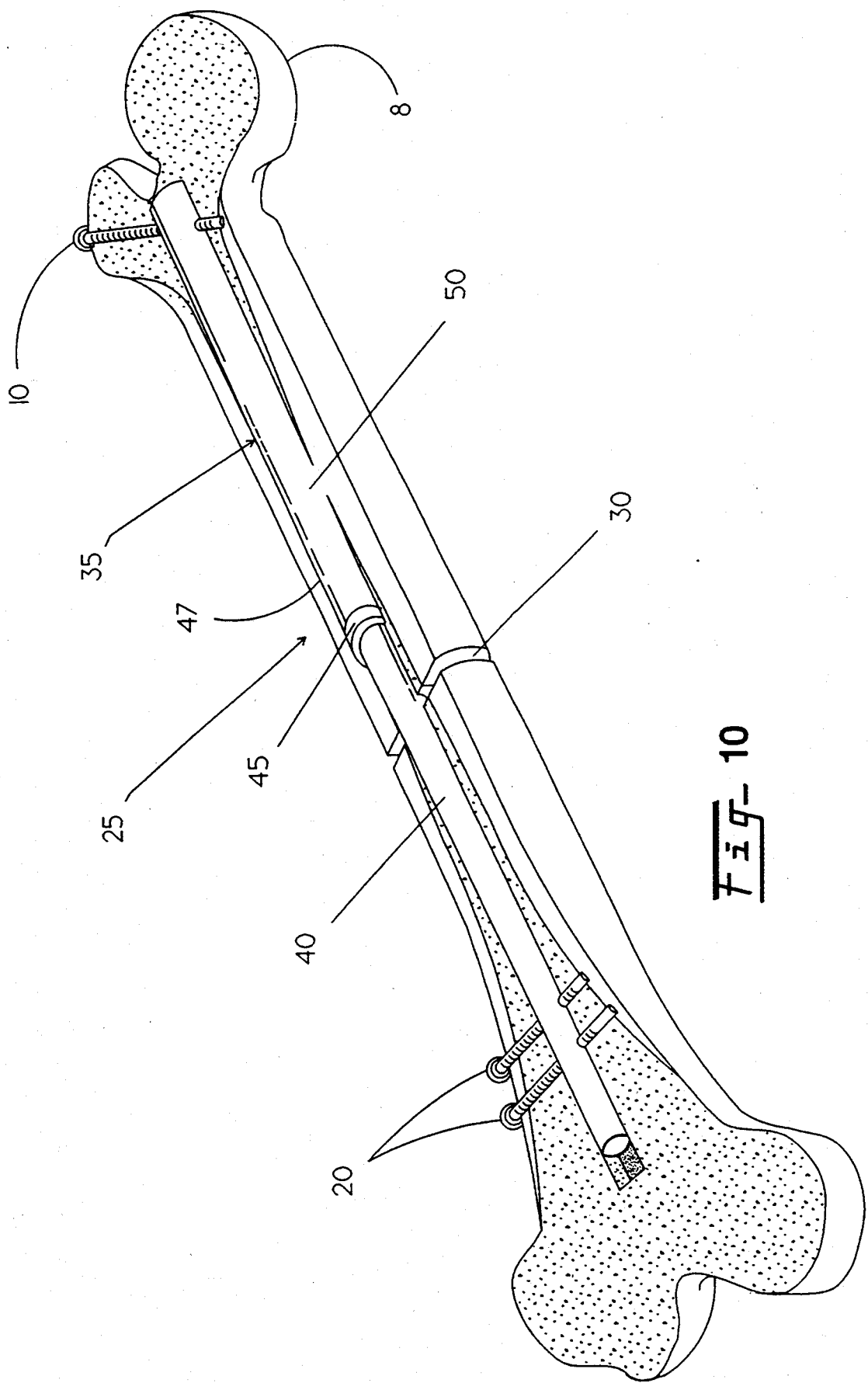
FIG. 10 shows a perspective view of one example embodiment of the invention employed within a bone.

FIG. 10 shows a perspective view of one example embodiment of the invention as employed within a bone 8. The intramedullary nail 25 is attached to the bone 8 by a proximal interlocking bolt 10 and distal interlocking bolts 20. An inner cylinder 40 and a telescoping outer cylinder 50 form the housing 35 of the intramedullary nail 25. A seal 45 seals the housing 35 preventing body fluids from entering the intramedullary nail 25, while allowing for expansion of the intramedullary nail 25. The outer cylinder 40 contacts the bone 8 along an isthmus 47 providing for improved stability. In one embodiment of the intramedullary nail apparatus, the inner cylinder 40, the telescoping outer cylinder 50, and the seal 45 form an sealed unit having no external connections. The bone 8 is cut at corticotomy site 30, allowing for expansion of the intramedullary nail 25, and distraction of the bone 8.

Figure 11:
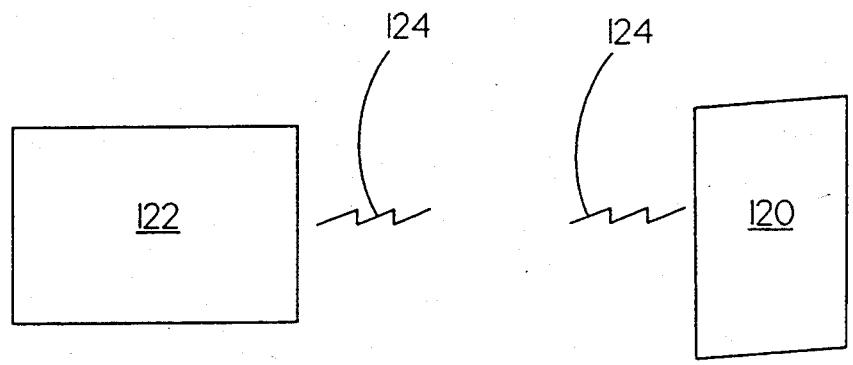
FIG. 11 shows a block diagram of one example of how telemetry may be used to initiate lengthening events.

FIG. 11 shows a block diagram of one example of how telemetry may be used to initiate lengthening events. In this example embodiment the invention has a telemetry apparatus 122 for sending a signal 124. A receiver 120 senses the signal 124 and initiates a lengthening event. Such telemetry units and receivers are commercially available and may be adapted for use with the present invention.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

I claim:

1. An implantable intramedullary bone lengthening apparatus, the apparatus comprising:
   a) an expandable housing means;
   b) a drive means employing a shape memory alloy attached to the expandable housing means for providing an expansion force; and
   c) an adjustment means for regulating and transmitting the expansion force, wherein the adjustment means is attached to the expandable housing means and the drive means, and wherein the adjustment means regulates and transmits the expansion force to expand the expandable housing means.

2. The implantable intramedullary bone lengthening apparatus of claim 1, wherein the expandable housing means further comprises an inner cylinder, a telescoping outer cylinder, and sealing means positioned between the inner cylinder and the telescoping outer cylinder for sealing a junction of the inner cylinder and the telescoping outer cylinder.

3. The implantable intramedullary bone lengthening apparatus of claim 2 wherein the sealing means further comprises at least one labyrinth seal.

4. The implantable intramedullary bone lengthening apparatus of claim 1, wherein the expandable housing means encloses the adjustment means and the drive means.

5. The implantable intramedullary bone lengthening apparatus of claim 1, wherein the expandable housing means encloses the adjustment means and the drive means so as to seal the adjustment means and drive means from body fluids.

6. The implantable intramedullary bone lengthening apparatus of claim 1, wherein the adjustment means comprises:
   a) a force transmission means for transmitting the expansion force provided by the drive means to the expandable housing means; and
   b) a ratcheting means for regulating a mechanical displacement of the expandable housing means.

7. The implantable intramedullary bone lengthening apparatus of claim 6 wherein the force transmission means further comprises a push rod attached to the expandable housing means.

8. The implantable intramedullary bone lengthening apparatus of claim 6 wherein the expandable housing means further comprises a proximal end and wherein the ratcheting means further comprises:
   a) a push rod positioned in the expandable housing means attached at one end to the proximal end;
   b) a plurality of fixed circular ledges attached along a length of the push rod; and
   c) a plurality of flexible elements attached along a length of an inner wall of the expandable housing means to engage the plurality of fixed circular ledges.

9. The implantable intramedullary bone lengthening apparatus of claim 8 wherein the plurality of flexible elements are positioned to engage the plurality of fixed circular ledges in staggered intervals.

10. The implantable intramedullary bone lengthening apparatus of claim 9 wherein at least one of the plurality of flexible elements simultaneously engage the plurality of fixed circular ledges in a load bearing position providing for stability.

11. The implantable intramedullary bone lengthening apparatus of claim 8 wherein the plurality of flexible elements further comprise a plurality of flexible rings inserted into a plurality of grooves along the length of the inner wall of the expandable housing means.

12. The implantable intramedullary bone lengthening apparatus of claim 11 wherein the plurality of flexible rings and the plurality of circular ledges are tapered to permit deflection of the plurality of flexible rings past the plurality of circular ledges.

13. The implantable intramedullary bone lengthening apparatus of claim 11 wherein the plurality of flexible rings each have a gap to provide for a pivoting action around the plurality of grooves of the inner wall of the expandable housing means and to permit deflection past the plurality of circular ledges.

14. The implantable intramedullary bone lengthening apparatus of claim 11 wherein the plurality of flexible rings each have offset radii to provide for a pivoting action around the plurality of grooves of the inner wall of the expandable housing means and to permit deflection past the plurality of circular ledges.

15. The implantable intramedullary bone lengthening apparatus of claim 6 wherein the expandable housing means further comprises a proximal end and wherein the ratcheting means further comprises:
   a) a push rod positioned in the expandable housing means attached at one end to the proximal end;
   b) a plurality of flexible elements attached along a length of the push rod; and
   c) a plurality of fixed circular ledges attached along a length of an inner wall of the expandable housing means to engage the plurality of flexible elements.

16. The implantable intramedullary bone lengthening apparatus of claim 15 wherein the plurality of flexible elements are positioned to engage the plurality of fixed circular ledges in staggered intervals.

17. The implantable intramedullary bone lengthening apparatus of claim 16 wherein at least one of the plurality of flexible elements simultaneously engage the plurality of fixed circular ledges in a load bearing position providing for stability.

18. The implantable intramedullary bone lengthening apparatus of claim 15 wherein the plurality of flexible elements further comprise a plurality of flexible rings inserted into a plurality of grooves along the length of the push rod.

19. The implantable intramedullary bone lengthening apparatus of claim 18 wherein the plurality of flexible rings and the plurality of circular ledges are tapered to permit deflection of the plurality of flexible rings past the plurality of circular ledges.

20. The implantable intramedullary bone lengthening apparatus of claim 18 wherein the plurality of flexible rings each have a gap to provide for a pivoting action around the plurality of grooves of the push rod and to permit deflection past the plurality of circular ledges.

21. The implantable intramedullary bone lengthening apparatus of claim 18 wherein the plurality of flexible rings each have offset radii to provide for a pivoting action around the plurality of grooves of the push rod and to permit deflection past the plurality of circular ledges.

22. An implantable intramedullary bone lengthening apparatus, the apparatus comprising:
   a) an expandable housing means;
   b) a shape memory driver for providing an expansion and displacement force located within and attached to the expandable housing means;
   c) a push collar located above the shape memory driver for providing a proximal and contracting force when forced upward by the expansion and displacement force from the shape memory driver;
   d) a wedge gripper located within the push collar for gripping an adjustment means and transmitting the expansion and displacement force to the adjustment means;
   e) biasing elements, for biasing the push collar toward the shape memory driver and for biasing the wedge gripper within the push collar; and
   f) a means for activating the shape memory driver connected to the shape memory driver.

23. The implantable intramedullary bone lengthening apparatus of claim 22 wherein the shape memory driver further comprises a shape memory tube driver.

24. The implantable intramedullary bone lengthening apparatus of claim 22 wherein the shape memory driver is connected to biasing elements that act to reset the shape memory driver.

25. The implantable intramedullary bone lengthening apparatus of claim 22 wherein the shape memory driver comprises a material having two-way thermal recovery properties.

26. The implantable intramedullary bone lengthening apparatus of claim 22 wherein the means for activating the shape memory driver further comprises:
   a) a telemetry means for sending a signal;
   b) a receiving means for receiving the signal from the telemetry means and sending an activation signal;
   c) a means for supplying power in response to the activation signal connected to receive the activation signal from the receiving means; and
   d) a means for heating connected to the means for supplying power and the shape memory driver for receiving power from the means for supplying power and for supplying heat to the shape memory driver.

27. The implantable intramedullary bone lengthening apparatus of claim 26 wherein the receiving means and the means for supplying power are implanted in soft tissues outside of the bone.

28. The implantable intramedullary bone lengthening apparatus of claim 26 wherein the means for supplying power comprises a battery.

29. The implantable intramedullary bone lengthening apparatus of claim 26 wherein the means for supplying power comprises a capacitor.

30. The implantable intramedullary bone lengthening apparatus of claim 26 wherein the means for supplying power comprises a capacitor wherein the capacitor may be charged by an inducted current.

31. The implantable intramedullary bone lengthening apparatus of claim 26 wherein the means for heating comprises a resistive wire wrapped around the shape memory driver.

32. The implantable intramedullary bone lengthening apparatus of claim 26 wherein the means for heating comprises a biocompatible alloy exhibiting a shape memory effect having resistive properties.

33. The implantable intramedullary bone lengthening apparatus of claim 26 wherein the means for heating comprises an inductive heating means for generating heat in the shape memory driver.

34. The implantable intramedullary bone lengthening apparatus of claim 22 wherein the shape memory driver comprises a biocompatible material exhibiting a shape memory effect.

35. The implantable intramedullary bone lengthening apparatus of claim 22 wherein the shape memory driver is a biocompatible alloy selected from the group consisting of nickel-titanium and nickel-titanium-copper.

36. The implantable intramedullary bone lengthening apparatus of claim 22 wherein the shape memory driver is an alloy exhibiting a shape memory effect selected from the group consisting of nickel-titanium, nickel-titanium-copper, and copper-zinc.

37. An implantable intramedullary bone lengthening apparatus, the apparatus comprising:
   a) an expandable housing means having an inner cylinder, a telescoping outer cylinder and a sealing means for sealing a junction of the inner cylinder and the telescoping outer cylinder;
   b) a drive means employing a shape memory alloy attached to the expandable housing means for providing an expansion force; and
   c) an adjustment means for regulating and transmitting the expansion force attached to the expandable housing means and the drive means, wherein the adjustment means regulates and transmits the expansion force to expand the expandable housing means, the adjustment means further comprising:
      i) a push rod having a plurality of grooves, attached to the telescoping outer cylinder;
      ii) a plurality of tapered flexible rings for attachment to the plurality of grooves, the plurality of tapered flexible rings having a smaller radius and a larger radius, the larger radius having a gap and being offset from the smaller radius, for permitting deflection of the plurality of tapered flexible rings around the plurality of grooves;
      iii) a plurality of circular ledges attached along an inner wall of the inner cylinder, spaced to engage the plurality of tapered flexible rings in a staggered pattern, and tapered to permit deflection of the plurality of tapered flexible rings past the plurality of circular ledges.

38. A ratcheting apparatus for regulating linear displacement within a narrow cavity, the ratcheting apparatus comprising:
   a) a first mounting and a second mounting slideably engaged to the first mounting;
   b) a plurality of fixed ledges attached to the first mounting; and
   c) a plurality of flexible rings having a gap wherein the plurality of flexible rings are attached to a second mounting, the plurality of flexible rings engaging the plurality of fixed ledges, wherein the gap permits deflection of the plurality of flexible rings past the plurality of fixed ledges.

39. The ratcheting apparatus of claim 38 wherein at least one of the plurality of flexible rings simultaneously engage the plurality of fixed ledges in a load bearing position providing for stability.

40. The ratcheting apparatus of claim 38, wherein the second mounting comprises a push rod, and wherein the plurality of flexible rings are inserted into a plurality of grooves on the push rod.

41. The ratcheting apparatus of claim 40 wherein the plurality of flexible rings and the plurality of circular ledges are tapered to permit deflection of the plurality of flexible rings past the plurality of circular ledges.

42. The ratcheting apparatus of claim 40 wherein the plurality of flexible rings each have a gap to provide for a pivoting action around the plurality of grooves of the push rod and to permit deflection of the plurality of flexible rings past the plurality of circular ledges.

43. The ratcheting apparatus of claim 40 wherein the plurality of flexible rings each have offset radii to provide for a pivoting action around the plurality of grooves of the push rod and to permit deflection of the plurality of flexible rings past the plurality of circular ledges.

44. The ratcheting apparatus of claim 38, wherein the plurality of flexible elements engage the plurality of fixed circular ledges in staggered intervals.

45. The ratcheting apparatus of claim 38, wherein the first mounting is adapted to be implanted in a bone.

* * * * *